(12) United States Patent
Benvegnu et al.

(10) Patent No.: US 8,569,467 B2
(45) Date of Patent: Oct. 29, 2013

(54) C-GLYCOSIDE COMPOUNDS, AND METHOD FOR PREPARING C-GLYCOSIDE COMPOUNDS

(75) Inventors: Thierry Benvegnu, Rennes (FR); Loïc Lemlegre, Rennes (FR); Adeline Ranoux, Clermont-Ferrand (FR)

(73) Assignees: Ecole Nationale Supérieure de Chimie de Rennes (FR); Armor Proteines (FR)

( * ) Notice: Subject to any disclaimer, the term of this patent is extended or adjusted under 35 U.S.C. 154(b) by 184 days.

(21) Appl. No.: 13/127,380

(22) PCT Filed: Nov. 6, 2009

(86) PCT No.: PCT/EP2009/064792
§ 371 (c)(1),
(2), (4) Date: Jun. 21, 2011

(87) PCT Pub. No.: WO2010/052314
PCT Pub. Date: May 14, 2010

(65) Prior Publication Data
US 2011/0245490 A1 Oct. 6, 2011

(30) Foreign Application Priority Data

Nov. 7, 2008 (FR) .................................. 08 57576
Nov. 26, 2008 (FR) .................................. 08 58024

(51) Int. Cl.
C07H 1/00 (2006.01)
C07H 3/00 (2006.01)
C08B 37/00 (2006.01)

(52) U.S. Cl.
USPC .......................... 536/1.11; 536/124

(58) Field of Classification Search
None
See application file for complete search history.

(56) References Cited

U.S. PATENT DOCUMENTS

2004/0048785 A1* 3/2004 Dalko et al. ................ 514/8

FOREIGN PATENT DOCUMENTS

WO 02051828 A 7/2002

OTHER PUBLICATIONS

International Search report and Written Opinion, dated May 6, 2010.
Aucagne, et al., "Synthetic Approaches to C-Glucosinolates" Tetrahedron, Elsevier Science Publishers, Amsterdam, NL, vol. 56, No. 17, Apr. 1, 2000, pp. 2647-2654.

* cited by examiner

Primary Examiner — Layla Bland
(74) Attorney, Agent, or Firm — Thomas Horstemeyer, LLP

(57) ABSTRACT

The invention relates to C-glycose compounds of formula (I) where: S' is a monosaccharide radical or a polysaccharide radical derived from a monosaccharide or polysaccharide S; R is a linear or branched alkyl radical; and Z is an ethylenyl $CH=CR1(R2)$ or an acetylenyl $C\equiv CR3$ radical. The invention also relates to a method for preparing C-glycoside compounds of formula (III), characterized in that the method consists of a step of reacting a sugar (S), in an aqueous solvent or in the absence of a solvent and in the presence of an organic or mineral base (B), with a phosphonate of formula (II) according to the following reaction pattern: Formulas (II), (III).

8 Claims, 1 Drawing Sheet

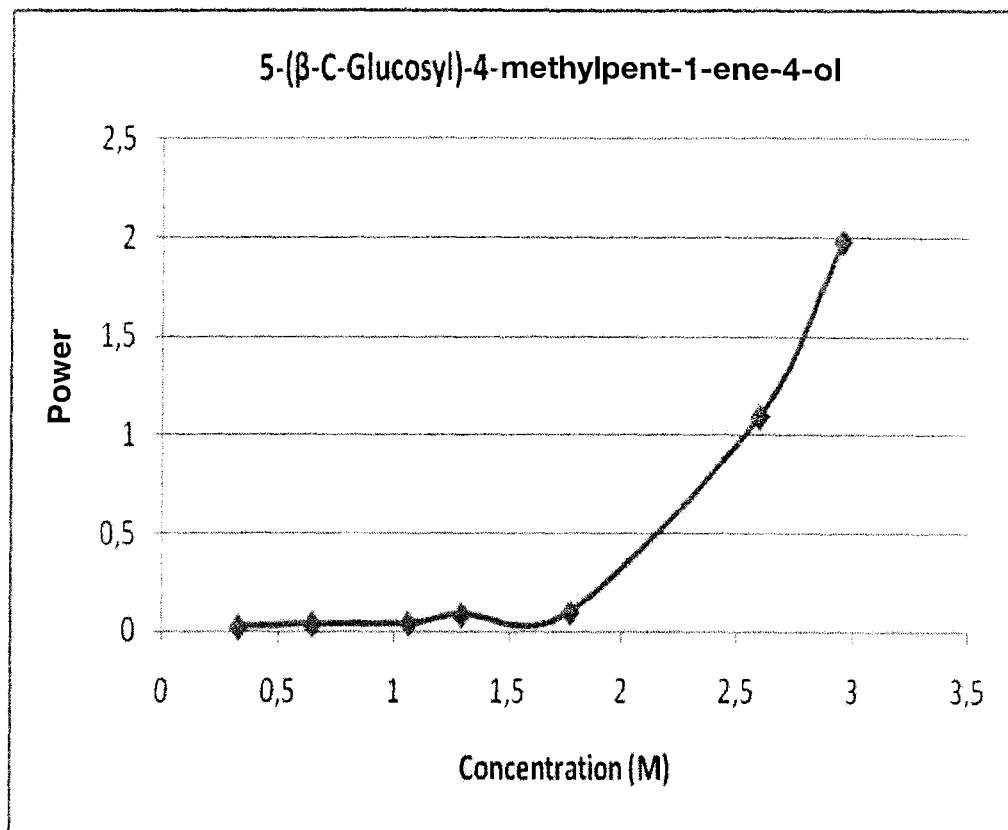

C-GLYCOSIDE COMPOUNDS, AND METHOD FOR PREPARING C-GLYCOSIDE COMPOUNDS

CROSS REFERENCE TO RELATED APPLICATION

This application claims priority to PCT Application entitled "C-Glycoside Compounds, and Method for Preparing C-Glycoside Compounds," having serial number PCT/EP2009/064792, filed on 6 Nov. 2009, which claims priority to and benefit of French Patent Application No. 0857576, filed on Nov. 7, 2008 and French Patent Application No. 0858024, filing date Nov. 26, 2008, both of which are incorporated by reference in their entirety.

The field of the invention is that of the synthesis of C-glycoside compounds. Such compounds are used in particular for producing compositions having surfactant properties and for producing cosmetic compositions.

More precisely, the invention concerns such C-glycoside compounds as well as various methods of preparing such compounds.

The chemical products industry is constantly seeking compounds that are environmentally friendly, in particular by being biodegradable and eco-compatible, as well as methods of synthesising such compounds best meeting the legal and regulatory provisions with regard to ecology.

Thus surfactant compounds based on sugar have many advantages. In particular, they are renewable, biodegradable, of low toxicity and afford original properties in particular with respect to substrates of petrochemical origin. Among these original properties, the very low potential for skin irritation and liquid crystalline properties, which afford sensory properties sought in cosmetics, can be cited.

Compounds based on sugars such alkyl polyglucosides (APGs), sorbitan esters and sugar esters have been developed. Even though these compounds have an obvious advantage for many applications, the search for novel molecules based on sugar remains an essential research field for improving the performances of surfactants.

The synthesis of surfactants from sugars is known through esterification, etherification, glycosidation or enzymatic synthesis. Some of these methods are based on the use of organic solvents and therefore do not entirely meet the concept of environmentally friendly chemistry.

Another method consisting of the synthesis of C-glycoside derivatives as a novel family of surfactants is described in the international application WO 02/051828. These compounds comprise a methylene group (C-glycoside) in place of the anomeric oxygen atom (O-glycoside). The mere replacement of an anomeric oxygen atom with a C-anomeric carbon atom can give rise to modifications to the physical and chemical properties, in particular the value of the CMC (critical micellar concentration), the interface tension, the hydrosolubility, the hydrophilic/lipophilic balance, the hydration and the liquid crystalline properties, among other things. One drawback of certain synthesis methods proposed in the application WO 02/051828 relates to the use of organic co-solvents, which is not sufficiently environmentally friendly.

There is therefore a need to have available novel surfactant compounds having improved performances and tolerances.

There is also a need to have available surfactant compounds meeting environmental standards such as biodegradability and eco-compatibility.

There is also a need to have available novel C-glycoside compounds having a wide field of application.

There is also a need to have available novel methods of preparing C-glycoside compounds that are more environmentally friendly.

The invention aims to meet all or some of these requirements.

C-glycoside Compounds of the Tertiary Alcohol Type

The subject matter of the invention, according to a first of the aspects thereof, is C-glycoside compounds having the following formula (I):

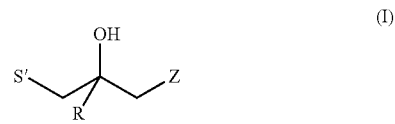

where:

S' represents a monosaccharide radical or polysaccharide radical having up to 20 sugar units, in pyranose and/or furanose form and of series L and/or D;

the bond S'—$CH_2C(OH)$ represents of bond of C-anomeric nature;

R represents a linear or branched alkyl radical that may have one or more insaturations, and comprising 1 to 30 carbon atoms; and Z represents an ethylenyl radical CH=CR1(R2) or acetylenyl radical C≡CR3 such that R1, R2 and R3 represent independently a hydrogen atom or a linear or branched alkyl radical, which may have one or more insaturations and comprising 1 to 30 carbon atoms.

The novel C-glycoside compounds of the tertiary alcohol type of formula (I) have high chemical and/or enzymatic stability, compatible with a wide range of applications.

Compared in particular with O-glycoside derivative analogues or analogues of esters or of esters derived from sugars, the C-glycoside derivatives according to the invention are able to have advantageous properties. In particular, the solubilising capacity thereof is able to be more effective and/or more specific according to the substrates. The hydrotropic capacity thereof or the ability thereof to stabilise formulations (cloud temperature) is also able to be better. The sensory properties thereof may be original, conferring in particular a rich, silky and non-fatty feel on cosmetic compositions.

Because of the presence of insaturations in the Z radical and/or the presence of a tertiary alcohol, the compounds according to the invention are able to have different physical and chemical properties from those of the prior art.

Preferentially, said S' radical is chosen from the group formed by the radicals: glucosyl, galactosyl, mannosyl, xylosyl, lactosyl, N-acetyl-glucosaminosyl and N-acetyl-galactosaminosyl.

In particular, said S' radical is advantageously chosen from the group formed by the radicals: lactosyl, glucosyl, xylosyl.

Equally preferentially, Z represents a radical $CH=CH_2$.

Method A: Method of Preparing C-glycoside Compounds of Formula (III)

Another subject matter of the invention, independently of or in combination with the above, is a method of preparing C-glycoside compounds of formula (III) including a step consisting of, in an aqueous solvent or in the absence of solvent and in the presence of an organic or mineral base B, causing a sugar S to react with a phosphonate of formula (II), in accordance with the following reaction diagram:

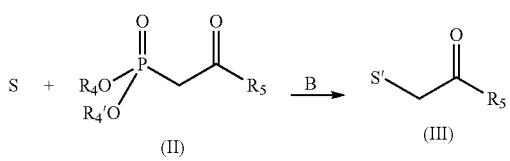

where:

S represents a monosaccharide radical or a polysaccharide radical having up to 20 sugar units in pyranose and/or furanose form and of series L and/or D, said mono- or polysaccharide having at least one free hydroxyl function;

S' represents a monosaccharide radical, or polysaccharide radical having up to 20 sugar units, in pyranose and/or furanose form and of series L and/or D derived from said monosaccharide or polysaccharide S;

the bond S'—$CH_2C(O)$ represents a bond of C-anomeric nature;

R4 and R4' represent independently a linear or branched alkyl radical comprising 1 to 6 carbon atoms, R5 represents an R, O—R, S—R or NH—R radical where R represents a linear or branched alkyl radical that may have one or more insaturations and comprising 1 to 30 carbon atoms.

It should be noted that, in the context of the present description, the monosaccharides or polysaccharides S used, apart from a free hydroxyl function, can moreover have one or more hydroxyl functions, protected or not, and/or one or more amine functions, protected or not.

According to a variant, B is preferentially a mineral base.

S can be chosen from the group formed by: glucose, galactose, mannose, xylose, lactose, N-acetyl-glucosamine and N-acetyl-galactosamine and the polysaccharides consisting of sugar units chosen from these.

S can in particular comprise lactose and/or glucose and/or xylose.

According to a variant R4 and R4' can in particular each represent a methyl radical $CH_3$.

The method according to the invention makes it possible to introduce a single chain in the anomeric position without causing oligomerisation of the sugar.

Variant A1 in the Presence of an Aqueous Solvent

Method A1 can, according to a variant A1, be used in an aqueous solvent, in particular in water.

In this case, the method can include the steps consisting of, in particular in the following order, dissolving an equivalent of said monosaccharide or polysaccharide S in a sufficient quantity of water;

adding between 1 and 5 equivalents of said phosphonate of formula (II) and between 1 and 10 equivalents of said base (B), at a temperature of between 25° C. and 100° C., over a period of between 3 hours and 30 hours;

neutralising the reaction medium by a mineral or organic acid or by passing an acid resin;

concentrating and then co-evaporating with an organic solvent chosen from the group consisting of ethanol, methanol, toluene and/or isopropanol, or drying, or freeze drying.

The method may also include the step consisting of purifying the reaction mixture obtained, by chromatography or crystallisation.

Variant A2 without Solvent

In another embodiment of the method, the method is implemented in the absence of any solvent.

In this case, the method may include the following step:

dissolving an equivalent of said monosaccharide or polysaccharide (S) and between 1 and 10 equivalents of base (B) in 3 to 25 equivalents of phosphonate of formula (II) at a temperature of between 25° C. and 100° C., in particular between 50° C. and 70° C., over a period of between 3 hours and 30 hours, in particular between 20 and 25 hours.

The method may also include the step consisting of distilling the reaction mixture obtained, the phosphonate then recovered being able to be recycled and engaged in a new reaction.

The method may also include the step consisting of purifying the product obtained by chromatography and/or crystallisation.

Method B: Method of Preparing C-glycoside Compounds of Formula (I) from C-glycoside Compounds of Formula (III')

Another subject matter of the invention, according to another of the aspects thereof, is a method of preparing C-glycoside derivatives of the tertiary alcohol type of formula (I) including a step consisting of making a C-glycoside compound of formula (III') react in an aqueous solvent and in the presence of a metal, with a halogenated compound of formula (IV) in accordance with the following reaction diagram:

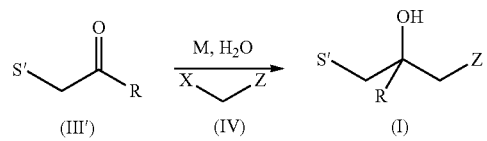

where:

S' represents a monosaccharide radical, or polysaccharide radical having up to 20 sugar units, in pyranose and/or furanose form and of series L and/or D derived from said monosaccharide or polysaccharide S;

the bond S'—$CH_2C(O)$ represents a bond of C-anomeric nature;

R represents a linear or branched alkyl radical, able to have one or more insaturations, and comprising 1 to 30 carbon atoms, and Z represents an ethylenyl radical CH=CR1(R2) or acetenyl radical C≡CR3 such that R1, R2 and R3 represent independently a hydrogen atom or a linear or branched alkyl radical, able to have one or more insaturations and comprising 1 to 30 carbon atoms;

M represents a metal chosen from indium, zinc or magnesium.

The method may thus include the steps consisting of, in particular in the following order:

dissolving an equivalent of said C-glycoside compound of formula (III') in a sufficient quantity of water;

adding between 1 and 4 equivalents of said halogenated compound of formula (IV) and between 1 and 4 equivalents of metal (M) at a temperature of between 20° C. and 40° C. over a period of between 3 hours and 30 hours; and co-evaporating the aqueous phase with an organic solvent chosen from the group consisting of ethanol, methanol, toluene and/or isopropanol, or drying, or freeze drying.

The method may also include the step consisting of washing the reaction mixture with an organic solvent such as dichloromethane or centrifuging with elimination of the deposit, after the dissolution step.

The method may also include the step consisting of purifying the obtained reaction mixture by chromatography and/or crystallisation.

The method may lead to the obtaining of a mixture composed, as a percentage by weight with respect to the whole of the mixture, of 0% to 30% C-glycoside compound of formula (III') and 50% to 100% of C-glycoside derivatives of formula (I).

Method C: Method of Preparing C-glycoside Compounds of Formula (I) from Sugar S

Another subject matter of the invention, according to another of the aspects thereof, is a method of preparing C-glycoside derivatives of the tertiary alcohol type of formula (I) consisting of making a sugar S react with a phosphonate of formula (II') in the presence of aqueous solvent, a metal M, in the presence of an organic or mineral base B, in particular mineral, and a halogenated compound of formula (IV), in accordance with the following reaction diagram:

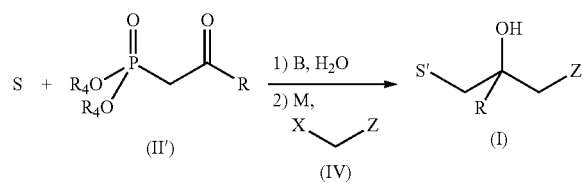

where:

S represents a monosaccharide or a polysaccharide having up to 20 sugar units, in pyranose and/or furanose form and of series L and/or D, said mono- or polysaccharide having at least one free hydroxyl function;

S' represents a monosaccharide radical, or polysaccharide radical having up to 20 sugar units, in pyranose and/or furanose form and of series L and/or D derived from said monosaccharide or polysaccharide S;

the bond S'—$CH_2C(OH)$ represents a bond of C-anomeric nature;

R4 and R4' represent independently a linear or branched alkyl radical comprising 1 to 6 carbon atoms;

R represents a linear or branched alkyl radical, which may have one or more insaturations, and comprising 1 to 30 carbon atoms; and X represents a halogen;

Z represents an ethylenyl function CH=CR1(R2) or acetylenyl function C≡CR3 such that R1, R2 and R3 represent independently a hydrogen atom or a linear or branched alkyl radical, able to have one or more insaturations and comprising 1 to 30 carbon atoms, and M represents a metal chosen from indium, zinc or magnesium.

The method according to the invention may include the following steps:

dissolving an equivalent of said monosaccharide or polysaccharide S in a sufficient quantity of water, adding between 1 and 5 equivalents, in particular between 2 and 3 equivalents, of phosphonate of formula (II'), and between 1 and 10 equivalents, in particular between 3 and 6 equivalents, of base B, at a temperature of between 25° C. and 100° C., in particular between 50° C. and 70°, over a period of between 3 hours and 30 hours, preferentially between 20 hours and 25 hours;

adding between 1 and 4 equivalents of said halogenated compound of formula (IV) and between 1 and 4 equivalents of metal (M) at a temperature of between 20° C. and 40° C. over a period of between 3 hours and 30 hours; and co-evaporating the aqueous phase with an organic solvent chosen from the group consisting of ethanol, methanol, toluene and/or isopropranol, or drying, or freeze drying, preferentially freeze drying directly.

The method may also include, after the addition step, the step consisting of washing the reaction mixture with an organic solvent, in particular dichloromethane, or centrifuging it with elimination of the deposit.

At the end, the method may include the step consisting of purifying the obtained reaction product obtained, by chromatography and/or crystallisation.

The method may lead to the obtaining of a mixture composed, as a percentage by weight with respect to the whole of the mixture, of 0% to 20% sugar S, 0% to 30% C-glycoside compound of formula (III') and 50% to 100% of C-glycoside derivative of formula (I).

According to one aspect of the invention, the saccharide S used in the context of the method according to this will be used in the form of a lactose juice. Such a lactose juice may for example come from the dairy industry.

Uses

The C-glycoside compounds of formula (III) and the C-glycoside compounds of formula (I) obtained by methods A, B and C described above are able to have in particular hydrotropic, solubilising, detergent or emulsifying properties and may thus be used in formulations for applications in washing, cosmetics, pharmacy and inks and paints, among other things.

The invention will be understood more clearly with reference to the description that follows of various example embodiments thereof.

EXAMPLES

Example 1

Method A1 in Water

Synthesis of 1-(C-Lactosyl)-propan-2-one 1 mmol of lactose and 9 mmol of $K_2CO_3$ (9 eq.) are dissolved in 2 ml of water heated to 65° C. 3 mmol of dimethyl-2-oxypropylphosphonate (3 eq.) are added. The reaction mixture is left under stirring for approximately 24 hours at 65° C. and is then neutralised by the addition of a 5% hydrochloric acid solution. After freeze drying, purification by chromatography column on silica gel (Eluent: AcOEt/MeOH/$H_2O$: 15/4/1) isolates the product in the form of a white solid with a 67% yield (β/α mixture: 90/10).

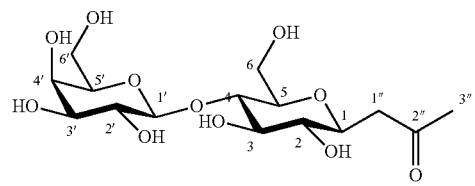

NMR: Majority Product 1"-(β-C-Lactosyl)-propan-2"-one:
$^1$H ($D_2O$) (400 MHz): δ (ppm): 2.23 (s, 3H, H-3"), 2.68 (d, 1H, J=9.52 Hz, J=17.04 Hz, H-1"b), 2.99 (d, 1H, J=2.88 Hz, J=17.04 Hz, H-1"a) 3.24 (t, 1H, J=9.28 Hz, H-2), 3.51 (dd, 1H, H-5'), 3.52 (dd, 1H, H-2'), 3.59 (dd, 1H, H-6'b), 3.62 (dd, 1H, H-3), 3.67 (td, 1H, H-5), 3.70 (dd, 1H, H-6'a), 3.73 (dd, 1H, H-4), 3.74 (dd, 1H, H-6b), 3.75 (dd, 1H, H-3'), 3.78 (td, 1H, H-1), 3.85 (dd, 1H, H-4'), 3.88 (dd, 1H, H-6a), 4.39 (d, 1H, J=7.72 Hz, H-1')

$^{13}$C (D$_2$O) (100 MHz): δ (ppm): 30.14 (C-3"), 45.93 (C-1"), 60.35 (C-6), 61.35 (C-6'), 68.85 (C-4'), 71.26 (C-2'), 72.81 (C-4), 73.06 (C-2), 75.35 (C-1), 75.65 (C-3'), 76.06 (C-3), 78.66 (C-5'), 78.68 (C-5), 103.21 (C-1'), 213.61 (C-2")

[α]$_D$=+4.14° (c=1, MeOH)

Infra-Red Spectroscopy:

(KBr) ν (cm$^{-1}$): 980-122 at (C—C, C—O stretch), 1705 (C=O), 1945 (C—H), 3050-3600 (O—H stretch)

Mass Spectrometry:

[M+Na]$^+$: theoretical m/z=405.13728; measured=405.1373

[M+K]$^+$: theoretical m/z=421.11122; measured=421.1127

Mass Spectrometry:

[M+Na]$^+$: theoretical m/z=299.14706; measured 299.1474

Example 3

Method A2 without Solvent

Synthesis of 1-(C-Lactosyl)-tridecan-2-one 1 mmol of lactose and 3 mmol of K$_2$CO$_3$ (3 eq.) are dissolved in 15 mmol of dimethyl-2-oxytridecylphosphonate (15 eq.) heated to 75° C. The reaction mixture is left under stirring for approximately 24 hours at 75° C. The remaining phosphonate is then distilled and can be recycled (60% of the phosphonate engaged). A mixture containing the product with residues of phosphonates and lactose is then obtained. Purification by chromatography column on silica gel (Eluent: AcOEt) isolates the product in the form of a white solid with a yield of 50% (β/α mixture: 55/45).

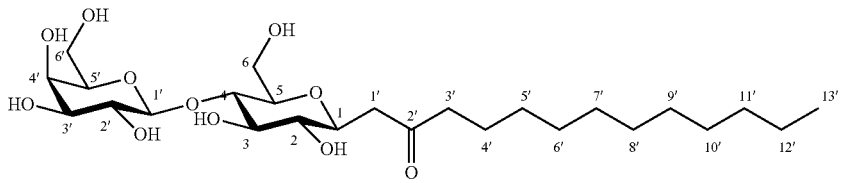

Example 2

Method A2 without Solvent

Synthesis of 1-(C-Glucosyl)-heptan-2-one 1 mmol of glucose and 3 mmol K$_2$CO$_3$ (3 eq.) are dissolved in 15 mmol of dymethyl-2-oxoheptylphosphonate (15 eq.) heated to 65° C. The reaction mixture is left under stirring for approximately 24 hours at 65° C. The remaining phosphonate is then distilled and can be recycled (70% of phosphonate engaged). A mixture containing the product with residues of phosphonates and lactose is then obtained. Purification by chromatography column on silica gel (Eluent: AcOEt/ MeOH/H$_2$O: 15/4/1) isolates the product in the form of a yellow solid with a yield of 45% (β/α mixture: 70/30).

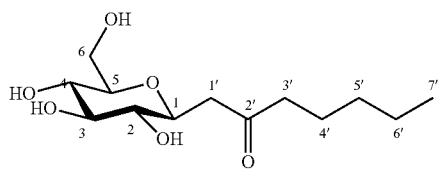

NMR: Majority Product 1'-(β-C-glucosyl)-heptan-2'-one $^1$H (CD$_3$OCD$_3$) (400 MHz): δ (ppm): 0.90 (3H, t, J=7.2 Hz, H-7), 1.29 (4H, m, H-5', H-6'), 1.51 (2H, q, J=7.2 Hz, H-4'), 2.49 (3H, m, H-3', H-1'a), 2.80 (1H, dd, J=15.6, 2.8 Hz, H-1'b), 3.08 (1H, t, J=8.8 Hz, H-2), 3.23 (1H, ddd, J=9.2, 5.2, 2.8 Hz, H-5), 3.33 (1H, t, J=8.6 Hz, H-4), 3.36 (1H, t, J=8.6 Hz, H-3), 3.59 (1H, dd, J=11.0, 5.2 Hz, H-6a), 3.68 (1H, td, J=9.6, 3.2 Hz, H-1), 3.70 (1H, d, J=10.8 Hz, H-6b)

$^{13}$C (CD$_3$OCD$_3$) (100 MHz): δ (ppm): 14.99 (C-7'), 23.92 (C-6'), 24.60 (C-5'), 32.82 (C-4'), 44.34 (C-3'), 47.03 (C-1'), 63.79 (C-6), 72.74 (C-4), 75.69 (C-2), 77.75 (C-1), 80.38 (C-3), 81.82 (C-5), 209.73 (C-2')

[α]$_D$=−15.9° (c=1, MeOH

NMR: Majority Product 1"-(β-C-lactosyl)-tridecan-2"-one:

$^1$H (CD$_3$OCD$_3$) (400 MHz): δ (ppm): 0.90 (3H, t, J=6.8 Hz, H-13"), 1.20 (16H, m), 1.45 (2H, m, H-4"), 2.42 (2H, t, J=5.6 Hz, H-3"), 2.51 (1H, dd, J=16, 9.2 Hz, H-1"a), 2.77 (1H, t, J=16, 2.8 Hz, H-1"b), 3.06 (1H, t, J=9.6 Hz, H-2), 3.47-3.73 (12H, m), 4.25 (1H, d, J=7.2 Hz, H-1')

$^{13}$C (CD$_3$OCD$_3$) (100 MHz): δ (ppm): 13.83 (C-13"), 22.89 (C-12"), 23.54 (C-4"), 28-32 (C5"-C11"), 42.76 (C-3"), 44.91 (C-1"), 61.05 et 61.48 (C-6 et C-6'), 68.83, 70.97, 71.11, 72.05, 73.23, 75.61, 76.19, 78.63, 79.32, 103.74 (C-1'), 212.16 (C-2")

Mass Spectrometry:

[M+Na]$^+$: theoretical m/z=545.29378; measured 545.2941

Example 4

Method B 1 mmol of 1-(C-lactosyl)-propan-2-one obtained according to example 1 is dissolved in 2 ml of water, and then 1.5 mmol (1.5 eq.) of allyl bromide and 1.4 mmol (1.4 eq.) of indium in powder form are added. The mixture is stirred for 24 hours at room temperature. Two types of processing are then possible:

1) Washing with CH$_2$Cl$_2$ is carried out (4*7 ml). The aqueous phase is concentrated in a rotary evaporator and then left for the freeze dryer. A chromatography column on silica gel is then effected (Eluent: AcOEt/MeOH/H$_2$O=15/4/1), the product is obtained in the form of a white solid with a yield of 85% (β/α mixture: 90/10).

2) The reaction mixture is centrifuged. After deposit removal, the aqueous phase is freeze dried. A mixture is then obtained of the following composition: 15% 3-(C-Lactosyl)-2-propanone, 85% 5-(C-Lactosyl)-4-methylpent-1-en-4-ol.

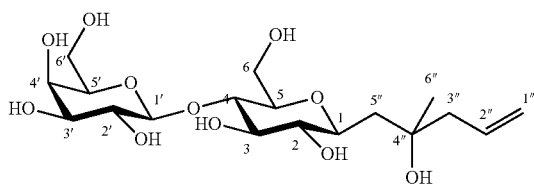

NMR: Majority Product: 5"-(β-C-Lactosyl)-4"-methylpent-1"-ene-4"-ol (diastereoisomers 1 and 2).

$^1$H (CD$_3$OD) (400 MHz): δ (ppm): 1.27 (s/s, 3H, H-6"1 et 2), 1.59 (dd, 1H, Jgem=14.8 Hz, J=9.28 Hz, H-5"), 1.98 (dd, 1H, Jgem=13.5 Hz, J=9.96 Hz, H-5"a), 3.08 (t, 1H, J=9.28 Hz, H-2), 2.25 (m, 2H, H-3" a et b), 3.26-3.38 (m, 2H), 3.43-3.60 (m, 4H), 3.66-3.88 (m, 3H), 4.32 (d/d, 1H, J=7.72 Hz, H-1'1 et H-1'2), 5.04 (m, 2H, J=14.84 Hz, H-1"a1/b1 et H-1"a2/b2), 5.86 (m, 1H, J=7.76 Hz, H-2"1 et H-2"2)

$^{13}$C (CD$_3$OD) (100 MHz): δ (ppm): 26.34 (C-6"), 42.57 (C-5"2), 43.14 (C-5"1), 47.44 (C-3"), 61.00 (C-6), 61.68 (C-6'), 69.33 (C-4'), 71.52 (C-2'), 73.73 (C-4), 74.40 (C-2), 76.91 (C-3'), 77.01 (C-1), 79.04 (C-3), 80.07 (C-5'), 80.10 (C-5), 104.09 (C-1'), 117.14 (C-1"), 134.76 (C-2")

[α]$_D$=+2.2° (c=1, MeOH)

Infrared Spectroscopy:

(KBr) ν (cm$^{-1}$): 988-1216 (C—C, C—O stretch), 1658 (C=C), 1935 (C—H), 3050-3600 (O—H stretch)

Mass Spectrometry:

[m+Na]$^+$: theoretical m/z=447.18423; measured=447.1893

Example 5

Method C

Direct synthesis of 5-(C-Glucosyl)-4-methylpent-1-ene-4-ol 1 mmol of glucose and 9 mmol of K$_2$CO$_3$ (9 eq.) are dissolved in 2 ml of water heated to 65° C. 3 mmol of dimethyl-2-oxopropylphosphonate (3 eq.) is added. The reaction mixture is left under stirring for approximately 24 hours at 65° C. and then 1.5 mmol (1.5 eq.) of allyl bromide and 1.4 mmol (1.4 eq.) of indium in powder form. The mixture is stirred for 24 hours at room temperature. Two types of processing are then possible:

1) Washing with CH$_2$Cl$_2$ is carried out (4*7 ml). The aqueous phase is concentrated in a rotary evaporator and then left for the freeze drier. A chromatographic column on silica gel is then effected (Eluent: AcOEt/MeOH/H$_2$O=15/4/1), the product is obtained in the form of a colourless oil with a yield of 67% (β/α mixture: 90/10).

2) The reaction mixture is centrifuged. After deposit removal, the aqueous phase is freeze dried. A mixture is then obtained of the following composition: 10% glucose, 23% 3-(C-glucosyl)-2-propanone, 67% 5-(C-Glucosyl)-4-methylpent-1-1-ene-4-ol.

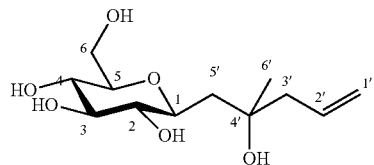

NMR: Majority Product 5'-(β-C-Glucosyl)-4'-methylpent-1'-ene-4'-ol (diastereoisomers 1 and 2)

$^1$H (CD$_3$OD) (400 MHz): δ (ppm): 1.29 (3H, s, H-6'), 1.69 (1H, m, H-5'b), 2.10 (1H, td, J=14.8, 2.4 Hz, H-5'a), 2.37 (2H, m, H-3'a, H-3'b), 3.12 (1H, t, J=8.8 Hz, H-2), 3.30-3.40 (3H, m, H-3, H-5, H-4), 3.54 (1H, tt, J=8.8, 2.4 Hz, H-1), 3.64 (1H, m, H-6b), 3.91 (1H, dt, J=12, 2.4 Hz, H-6a), 5.20 (1H, m, H-1'), 6.04 (1H, m, H-2')

$^{13}$C (CD$_3$OD) (100 MHz): δ (ppm): 27.93 (C-6'), 44.27 (C-5'), 48.43 (C-3'), 63.51 (C-6), 72.41 (C-4), 76.10 (C-2), 78.66 (C-1), 80.05 (C-3), 81.89 (C-5), 118.60 (C-2'), 136.19 (C-1')

[α]$_D$=+5.40° (c=1, MeOH)

Infrared Spectroscopy:

(Nujol) ν (cm$^{-1}$): 986-1215 (C—C, C—O stretch), 1655 (C=C), 1940 (C—H), 3050-3600 (O—H stretch)

Mass Spectrometry:

[M+Na]: theoretical m/z=285.13141; measured 285.1313

Tensiometric measurements, namely the measurement of the CMC (Critical Micelle Concentration) and the MAC (Minimal Aggregation Concentration) were made on various compounds obtained according to the invention.

The results of these measurements appear in table 1 below.

TABLE 1

The values obtained are characteristic of a good surfactant activity. According to the chain lengths, they are characteristic of compounds having hydrotropic, detergent or emulsifying properties.

| C-Glycoside compounds | CMC*/MAC** (mM) | $γ_{CMC/MAC}$*** (Mn · m$^{-1}$) |
|---|---|---|
| 5-C(Glucosyl)-4-methylpent-1-ene-4-ol | 350 | 34 |
| 1-C-(Lactosyl)-heptan-2-one | 17 | 30 |
| 1-C-(Glucosyl)-heptan-2-one | 18 | 30 |
| 1-C-(Galactosyl)-heptan-2-one | 17.5 | 30 |
| 1-C-(Glucosyl)-heptan-2-one | 0.2 | 28 |

*CMC: Critical Micelle Concentration
**MAC: Minimum Aggregation Concentration
***$γ_{CMC/MAC}$: Interface tension at the CMC/MAC The solubilising capacity of 5-β-C-Glucosyl)-4-methylpent-1-ene-4-ol was also assessed.

To test the solubilisation potential of the products, the dye Disperse Red 13, the maximum absorption band of which is at 525 nm, was used.

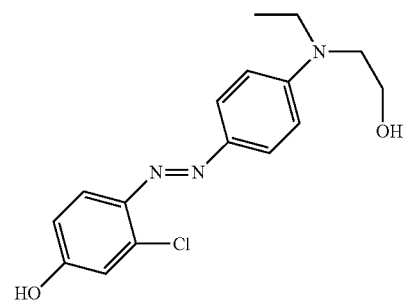 [SMILES: CCN(CCO)c1ccc(/N=N/c2ccc(O)cc2Cl)cc1]

Disperse Red DR13

Various solutions with a decreasing concentration of C-glycoside compound 5-((β-C-Glucosyl)-4-methylpent-1-ene-4-ol were prepared and a sufficient quantity of DR 13 (up to saturation of the solution) was dissolved. The absorbency of the solutions obtained was measured by UV absorption spectrometry at the wavelength of the dye, thus making it possible to quantify the solubilisation thereof. The results of these measurements appear in FIG. 1.

According to the interpretation that can be made of this FIGURE, 5-(β-C-Glucosyl)-4-methylpent-1-ene-4-ol has a good solubilising capacity, since the quantity of agent solubilised is high at a low concentration of solubilising agent.

Finally, the effects of various C-glycoside compounds obtained according to the invention on the cloud temperature of a surfactant were tested in order to evaluate the advantage thereof for the stabilisation of the formulations.

The surfactant taken as a reference is C6E2, diethylene glycol monohexylether. The results obtained appear in table 2 below.

TABLE 2

| Product(s) (% weight) | Cloud temp (° C.) |
|---|---|
| C6E2 (1%) | 34 |
| C6E2 (1%) + 5-C-(Glucosyl)-4-methylpent-1-ene-4-ol (10%) | 44 |
| C6E2 (1%) + 5-C-(Galactosyl)-4-methylpent-1-ene-4-ol (10%) | 42 |
| C6E2 (1%) + 5-C-(Lactosyl)-4-methylpent-1-ene-4-ol (10%) | 39 |
| C6E2 (1%) + 5-C-(Glucosyl)-4-heptan-2-one (1%) | 62 |
| C6E2 (1%) + 5-C-(Lactosyl)-4-heptan-2-one (1%) | 58 |

An increase in the cloud temperature of the surfactant C6E2 is observed through the addition of 10% (methylpent-1-ene-4-ol chain) or 1% (hepta-2-one chain) of product. The products according to the invention stabilise the formulations according to the temperature and can be used as co-surfactants.

The 5-(β-C-Glucosyl)-4-methylpent-1-ene-4-ol according to the present invention was used in the following two formulations:

| Composition formulation of a liquid soap | % by weight |
|---|---|
| 5-(β-Glucosyl)-4-methylpent-1-ene-4-ol | 5 |
| PPG-14 palmeth-60 alkyl dicarbamate | 3 |
| PEG-200 | 3 |
| Ethanol | 3 |
| Decyl glucoside | 20 |
| EDTA | 0.2 |
| Triethanolamine | 0.5 |
| Water | |

| Composition formulation of a detergent for cleaning smooth surfaces | % by weight |
|---|---|
| 5-(β-Glucosyl)-4-methylpent-1-ene-4-ol | 2 |
| 1-C-(Glucosyl)-heptan-2-one | 3 |
| 1-C-Glucosyl-tridecan-2-one | 3 |
| Sodium dodecyl sulfate | 0.3 |
| Ethanol | 3 |
| Essential oil of lemon 9286 (OSF) | 0.5 |
| Preservative | 0.4 |
| Water | |

The invention claimed is:

1. C-glycoside compound, characterised in that it has the following formula (I):

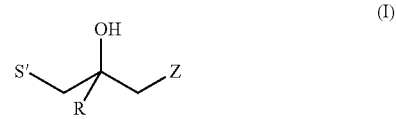

where:
S' represents a monosaccharide radical, or polysaccharide radical having up to 20 sugar units, in pyranose and/or furanose form and of series L and/or D:
the bond S'—$CH_2C(OH)$ represents a bond of a C-anomeric nature;
R represents a linear or branched alkyl radical able to have one or more insaturations and comprising 1 to 30 carbon atoms; and
Z represents an ethylenyl radical CH=CR1(R2) or acetylenyl radical C≡CR3 such that R1, R2 and R3 represent independently a hydrogen atom or a linear or branched alkyl radical, which may have one or more insaturations and comprising 1 to 30 carbon atoms.

2. Compound according to claim 1, in which said radical S' is chosen from the group consisting of the radicals: glucosyl, galactosyl, mannosyl, xylosyl, lactosyl, N-acetyl-glucosaminosyl, and N-acetyl-galactosaminosyl.

3. Compound according to claim 2, in which said radical S' is chosen from the group formed by the radicals: lactosyl, glucosyl, xylosyl.

4. Compound according to claim 1, characterised in that Z represents a CH=$CH_2$ radical.

5. Method of preparing C-glycoside compounds of the tertiary alcohol type of formula (I) including a step of making a C-glycoside compound of formula (III') react in an aqueous solvent and in the presence of a metal (M), with a halogenated compound of formula (IV) according to the following reaction diagram:

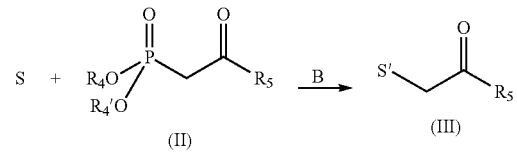

where:
S' represents a monosaccharide radical, or a polysaccharide radical having up to 20 sugar units, in pyranose and/or furanose form and of series L and/or D;
the bond S'—C $H_2C(O)$ represents a bond of C-anomeric nature;
R represents a linear or branched alkyl radical that may have one or more insaturations and comprising 1 to 30 carbon atoms;
Z represents an ethylenyl radical CH=CR1(R2) or acetylenyl radical C≡CR3 such that R1, R2 and R3 represent independently a hydrogen atom or a linear or branched alkyl radical, which may have one or more insaturations and comprising 1 to 30 carbon atoms;
M represents a metal chosen from indium, zinc or magnesium;
and X represents a halogen.

6. Method according to claim 5, characterised in that it comprises the steps consisting of:
- dissolving an equivalent of said C-glycoside compound of formula (III') in a sufficient quantity of water;
- adding between 1 and 4 equivalents of said halogenated compound of formula (IV) and between 1 and 4 equivalents of metal (M) at a temperature of between 20° C. and 40° C. over a period of between 3 hours and 30 hours; and
- co-evaporating the aqueous phase with an organic solvent chosen from the group formed by ethanol, methanol, toluene and/or isopropanol,
- or drying,
- or freeze drying.

7. Method of preparing C-glycoside compounds of the tertiary alcohol type of formula (I) comprising making a monosaccharide or a polysaccharide S react with a phosphonate of formula (II') in the presence of water, a metal (M) with a halogenated compound of formula (IV), in accordance with following reaction diagram:

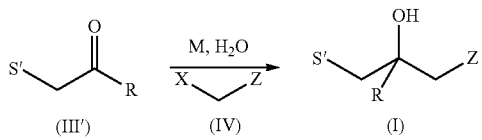

(III')   (IV)   (I)

where:
- S represents a monosaccharide or a polysaccharide having up to 20 sugar units, in pyranose and/or furanose form and of series L and/or D, said mono- or polysaccharide having at least one free hydroxyl function;
- S' represents a monosaccharide radical, or polysaccharide radical having up to 20 sugar units, in pyranose and/or furanose form and of series L and/or D derived from said monosaccharide or polysaccharide S;
- the bond S'—CH$_2$C(OH) represents a bond of C-anomeric nature;
- R4 and R4' represent independently a linear or branched alkyl radical comprising 1 to 6 carbon atoms;
- R represents a linear or branched alkyl radical, which may have one or more insaturations and comprising 1 to 30 carbon atoms;
- X represents a halogen,
- Z represents an ethylenyl function CH=CR1(R2) or acetylenyl function C≡CR3 such that R1, R2 and R3 represent independently a hydrogen or a linear or branched alkyl radical, which may have one or more insaturations and comprising 1 to 30 carbon atoms; and
- M represents a metal chosen from indium, zinc or magnesium; and
- B is an organic or mineral base.

8. Method according to claim 7, characterised in that it includes the steps consisting of:
- dissolving an equivalent of said monosaccharide or polysaccharide S in a sufficient quantity of water;
- adding between 1 and 5 equivalents, of phosphonate of formula (II'), and between 1 and 10 equivalents, of base B, at a temperature of between 25° C. and 100° C., over a period of between 3 hours and 30 hours;
- adding between 1 and 4 equivalents of said halogenated compound of formula (IV) and between 1 and 4 equivalents of metal (M) at a temperature of between 20° C. and 40° C. over a period of between of between 3 hours and 30 hours; and
- co-evaporating the aqueous phase with an organic solvent chosen from the group consisting of ethanol, methanol, toluene and/or isopropanol,
- or drying,
- or freeze drying.

* * * * *

UNITED STATES PATENT AND TRADEMARK OFFICE
CERTIFICATE OF CORRECTION

PATENT NO.        : 8,569,467 B2                                              Page 1 of 1
APPLICATION NO.   : 13/127380
DATED             : October 29, 2013
INVENTOR(S)       : Benvegnu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 227 days.

Signed and Sealed this
Twenty-second Day of September, 2015

Michelle K. Lee
*Director of the United States Patent and Trademark Office*